United States Patent [19]

Sinclair

[11] Patent Number: 5,096,715
[45] Date of Patent: * Mar. 17, 1992

[54] METHOD AND MEANS FOR TREATING ALCOHOLISM BY EXTINGUISHING THE ALCOHOL-DRINKING RESPONSE USING A TRANSDERMALLY ADMINISTERED OPIATE ANTAGONIST

[75] Inventor: John D. Sinclair, Espoo, Finland

[73] Assignee: Alko Ltd., Helsinki, Finland

[*] Notice: The portion of the term of this patent subsequent to Nov. 21, 2006 has been disclaimed.

[21] Appl. No.: 439,050

[22] Filed: Nov. 20, 1989

[51] Int. Cl.⁵ ............................................ A61F 13/00
[52] U.S. Cl. .................................... 424/449; 424/443; 424/444; 514/810; 514/811
[58] Field of Search ................. 424/449; 514/282, 811

[56] References Cited

U.S. PATENT DOCUMENTS

| 2,837,881 | 6/1958 | Schneider | 53/21 |
| 3,249,109 | 5/1966 | Maeth | |
| 3,966,940 | 6/1976 | Pachter et al. | 424/260 |
| 4,351,337 | 9/1982 | Sidman | 128/260 |
| 4,573,995 | 3/1986 | Chen | 604/896 |
| 4,626,539 | 12/1986 | Aungst | 514/282 |
| 4,629,539 | 12/1986 | Aungst et al. | 514/282 |
| 4,645,502 | 2/1987 | Gale | 604/896 |
| 4,680,172 | 7/1987 | Leeson | 424/449 |
| 4,806,341 | 2/1989 | Chien | 424/448 |
| 4,818,540 | 4/1989 | Chien | 424/448 |
| 4,882,335 | 11/1989 | Sinclair | 514/282 |

FOREIGN PATENT DOCUMENTS

| 019,423 | 11/1980 | Europe . |
| 84/00889 | 3/1984 | International . |
| 171,742 | 2/1986 | Europe . |
| 2,174,605A | 11/1986 | Great Britian . |
| 3,545,926 | 7/1987 | German . |
| 0267617 | 5/1988 | European Pat. Off. . |
| 0282156 | 9/1988 | European Pat. Off. . |
| 346,830 | 12/1989 | Europe . |

OTHER DOCUMENTS

Samson et al, *Pharmacology, Biochemistry & Behavior,* 22, No. 1, pgs. 91–99 (1985)
Sinclair et al, *British J. Addiction,* 82, No. 1, pgs. 1213–1223 (1987)
Marfaing-Jallat et al, *Pharmacology, Biochemistry & Behavior,* 18, Suppl. 1, pgs. 537–539 (1983)
Blum et al, *Nature,* 265, pgs. 49–51 (1977)
Sinden et al, *Pharamacology, Biochemistry & Behavior,* 19, No. 6, pgs. 1045–1048 (1983)
Altshuler et al, *Life Sciences,* 26, No. 9, pgs. 679–688 (1980)
Kotlinska et al, *Alcohol and Alcoholism,* 22, No. 2, pgs. 117–119 (1987)
Myers et al, *Alcohol,* 3, No. 6, pgs. 383–388 (1986)

(List continued on next page.)

*Primary Examiner*—Thurman K. Page
*Assistant Examiner*—James M. Spear
*Attorney, Agent, or Firm*—Armstrong, Nikaido, Marmelstein, Kubovcik & Murray

[57] ABSTRACT

A method for treating alcoholism by extinguishing the alcohol-drinking response in which an opiate antagonist is transdermally administered to a subject and a device for transdermally administering the antagonist. The device is a package containing a fixed dose of opiate antagonist, a vehicle and a permeation enhancer.

12 Claims, 1 Drawing Sheet

OTHER PUBLICATIONS

Cugurra, *La Clinica Terapeutica*, 127, No. 3, pgs. 173-180 (1988)

P.F. Renault, *NIDA Research Monograph*, 28, pgs. 11-12 (1981)

Childress et al, *International J. of the Addictions*, 20, No. 6/7, pgs. 947-969 (1985)

METHOD AND MEANS FOR TREATING ALCOHOLISM BY EXTINGUISHING THE ALCOHOL-DRINKING RESPONSE USING A TRANSDERMALLY ADMINISTERED OPIATE ANTAGONIST

BACKGROUND OF THE INVENTION

This invention relates to the treatment of alcoholism and particularly to an extinction method of treating alcoholism using a transdermally administered opiate antagonist. The invention also relates to a device for the rapid, transdermal administration or delivery of a fixed dose of the opiate antagonist.

A method for treating alcoholism by extinguishing the alcohol-drinking response is described in copending United States patent application Ser. No. 205,758, the disclosure of which is incorporated herein in its entirety by reference. In this extinction method, an opiate antagonist is administered to a subject suffering from alcoholism in a daily dosage sufficient to block the stimulatory effect of alcohol and, while the amount of antagonist in the subject's body is sufficient to block the stimulatory effect of alcohol, the subject is made to drink an alcoholic beverage. The steps of administration of the opiate antagonist and drinking of an alcoholic beverage are continued until the alcohol-drinking response is extinguished.

Existing methods for administering opiate antagonists, however, are inadequate for use in the extinction of the alcohol-drinking response.

Injection produces a strong stimulus which, together with any lingering irritation, would clearly distinguish the extinction sessions from normal alcohol drinking. The presence of such stimuli are known to interfere with the process of extinction (David W.M. and Smith, S.G. *Biological Psychiatry* 9: 181-189, 1974). Injection also reduces motivation and the willingness of the patient to remain in the treatment, which is an important consideration in alcoholism treatment.

Oral administration has the problem that compliance is difficult to assure, whereas it is essential in the extinction process that the alcoholic actually takes the antagonist before each session. Furthermore, oral administration currently can only be used with the antagonist naltrexone, and naltrexone has two disadvantages. First, it is a major liver toxin, which excludes it being used with many alcoholics. Second, it has such a long half-life in the body that there would still be active quantities present long after the end of a session. In order to avoid extinction of responses other than alcohol drinking, and to allow the other responses that are weakened during a session to regain their strength between sessions, it is desirable to restrict the presence of the antagonist as much as possible to the sessions, i.e., to the few hours in a day when the alcoholic is permitted to drink alcohol. Consequently, both a low build up of the antagonist in the body before a session and its continued presence after the session should be avoided as much as possible.

Transdermal administration can avoid these problems. It is painless and produces no clear stimulus provided that transdermal patches are not needed. Compliance is easy to monitor. Moreover, such administration can deliver naloxone which has a desirably short half-life for use in extinction. Transdermal devices previously disclosed for administering opiate antagonists, however, are not suitable for use in alcoholics for extinguishing the alcohol-drinking response.

All but one of the transdermal devices disclosed for administering opiate antagonists are patches. The presence of a patch would likely act as a stimulus present during the extinction sessions distinguishing them from normal drinking, and thus reducing the effectiveness of the extinction process. Furthermore, the disclosed transdermal patches do not generally provide sufficiently rapid delivery for use in the extinction procedure.

Three of the transdermal devices for opiate antagonists (Gale et al, U.S. Pat. No. 4,645,502, issued Feb. 24, 1987; Leeson, U.S. Pat. No. 4,680,172, issued July 14, 1987; and Chien et al, U.S. Pat. No. 4,806,341, issued Feb. 21, 1989, and related patents in other countries) are "system controlled" transdermal patches. That is, the patches contain a mechanism restricting and controlling the rate at which the antagonist is delivered. This prevents an initially high rate of delivery when the patch is first applied and allows long-term, sustained delivery at a relatively steady rate.

System-controlled devices are superior for most uses. For example, such devices would be preferred in the previously envisioned use of opiate antagonists to prevent the taking of narcotics (see NIDA Research Monograph No. 28, 1982). It was hypothesized that if addicts could be kept continually on an opiate antagonist, which blocks the pleasure from narcotics, the addicts would behave rationally and refrain from taking narcotics. Consequently, much work was done to try to find sustained delivery methods for antagonists that would supply constant amounts for very long periods of time. Sustained release is, however, neither necessary nor preferable for the delivery of antagonists in the extinction procedures. Because of the relatively wide therapeutic window, it is not necessary to keep the delivery rate constant. The added mechanisms in these devices to control the delivery rate, in addition to making them more complicated and expensive than necessary for use in the extinction procedure, also cause the time required to build up active quantities of antagonist to be unacceptably long and preclude delivery of the highest doses specified for the extinction procedure (e.g., 30 mg of naloxone.)

The device disclosed by Gale et al, U.S. Pat. No. 4,645,502, has only 30 $\mu g/cm^2/hr$ as the highest mentioned delivery rate, are fabricated in sizes up to only 40 $cm^2$ (thus giving a maximum delivery rate of 1.2 mg/hr), and has a lag time of 2-7 hours. The device disclosed by Leeson, U.S. Pat. No. 4,680,172, administers naloxone "at a rate of 0.01 to 5 mg/hr, preferably 0.02 to 2 mg/hr." Chien et al, U.S. Pat. No. 4,806,341, disclose no information about the rates for delivery of naloxone or other antagonists. The maximum rates shown for hydromorphone, up to about 100 $\mu g/cm^2/hr$ approach those needed for naloxone in the extinction procedure if a sufficiently large patch is used, but the only size mentioned, 10 $cm^2$, would deliver only 1 mg/hr. In contrast a device for use in the extinction procedure should be capable of delivering a minimum of 6 mg and, preferably, 9 mg or more of an opiate angatonist in an hour.

Two other transdermal patch devices have been disclosed that are "skin-controlled", i.e., they do not have an added mechanism for restricting delivery, but they also do not provide a rate of delivery high enough to be used in the extinction procedure. Maeth et al, U.S. Pat.

No. 3,249,109, issued May 3, 1966, discloses a topical dressing for applying medicaments or therapeutic agents through the skin. The patent, however, does not suggest the use of any permeation enhancer, i.e., a substance to increase the rate of diffusion of the drug across the skin. In the absence of such enhancers, the absorption of naloxone or naltrexone is not sufficient for systemic delivery of therapeutic doses.

Cheng et al, U.S. Pat. No. 4,573,995, issued Mar. 4, 1986, discloses a transdermal patch for the bases of naloxone and related drugs, with the permeation enhancer polyethylene glycol monolaurate. The highest mentioned flux was only 30.58 $\mu g/cm^2/hr$, although rates of up to 40 $\mu g/cm^2/hr$ are claimed.

Another transdermal means for delivering opiate antagonists is disclosed in Aungst et al, U.S. Pat. No. 4,626,539, issued Dec. 2, 1986. Vehicles and enhancers capable of delivering opiate antagonists at rates sufficient for use in the extinction procedure, e.g., several combinations produce rates for naloxone of over 300 $\mu g/cm^2/hr$, are described. A transdermal patch is mentioned. The preferred means, however, are lotions and creams. These means are inadequate for use by alcoholics because of the difficulty in controlling the total dose applied. The dose could be determined by squeezing a cylinder of a specified length out of a tube, as is done, e.g., with the transdermal delivery of nitroglycerin. This method, however, would not be appropriate for an alcoholic to self-administer an antagonist: unless there was very strict supervision, the risk of underdosing or overdosing would be too high. Most alcoholism treatment centers do not have sufficient staff for such strict supervision. For these centers and to simplify the procedure for use in all centers, it is necessary to have a device that reliably delivers a fixed dose of the antagonist. The device should be simple to use, as foolproof as possible, and inexpensive to manufacture.

SUMMARY OF THE INVENTION

According to the present invention, a method for treating alcoholism by extinction of the alcohol-drinking response is provided which comprises administering an opiate antagonist to a subject suffering from alcoholism in a daily dosage sufficient to block the stimulatory effect of alcohol and, while the amount of antagonist in the body of the subject is sufficient to block the stimulatory effect of alcohol, having the subject drink an alcoholic beverage, and continuing the steps of administering the opiate antagonist and drinking an alcoholic beverage by the subject until the alcohol-drinking response is extinguished, and wherein the opiate antagonist is administered by transdermal delivery with a means for delivery containing a fixed dose of the antagonist, a vehicle and a permeation enhancer.

According to a further embodiment of the invention a transdermal means for use in a method of extinction of the alcohol-drinking response is provided which comprises a fixed dose of an opiate antagonist in combination with a vehicle and a permeation enhancer capable of providing a diffusion rate high enough to deliver quantities of antagonist sufficient for the extinction procedure.

DESCRIPTION OF PREFERRED EMBODIMENTS

Figure 1A:
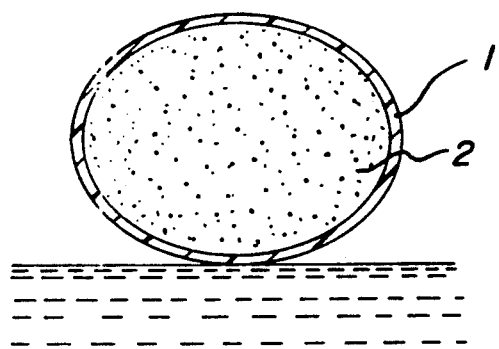
FIG. 1 shows a cross-sectional view of one embodiment of a transdermal device according to the present invention in the form of a capsule.

The extinction procedure can be used in all individuals classified by any of various means as alcoholics or alcohol abusers, except those in which the administration of an opiate antagonist is contraindicated and those suffering from Korsakoff's syndrome. (The extinction procedure would probably work poorly in patients with Korsakoff's syndrome).

The patients can be interviewed to determine the alcoholic beverages they usually drink and the drinking situations in which they normally imbibe. They can then be informed that unlike most treatments, this one does not involve immediately becoming abstinent; instead, their alcohol drinking is to be slowly diminished over many days and only after that will they have to abstain. This procedure should also help to reduce the severity of withdrawal symptoms that are often produced by abrupt termination of alcohol intake.

The patient can then have an opiate antagonist administered shortly before beginning to drink an alcoholic beverage. Examples of suitable opiate antagonists are naloxone, naltrexone, cyclazocine, diprenorphine, etazocine, levalorphan, metazocine, nalorphine, and their salts. The preferred opiate antagonists are naloxone and naltrexone, both of which have been approved for use in humans and have been shown to be free of severe side-effects. The dose administered in a specific case will depend upon the age and weight of the patient, the frequency of administration, and the route of administration, but must be sufficient to assure that the antagonist will be present in sufficient quantities in the body throughout the entire evening of alcohol drinking. The preferred dose range for naloxone using transdermal delivery according to the present invention is 0.2 to 40 mg daily. The preferred dose range for naltrexone using transdermal delivery according to the present invention is 20 to 300 mg daily. The first extinction session (i.e., drinking after administration of the antagonist) can be conducted under close supervision in the treatment center. It is important that later extinction sessions be conducted in the same drinking situations and with the same alcoholic beverages that the patient usually has employed in the past. The stimuli from these specific beverages and situations help to elicit somewhat separate alcohol-drinking responses for the individual. For example, in a particular alcoholic, the alcohol-drinking response of drinking beer while watching a game on TV may be at least partly independent of his responses of imbibing cocktails at a party or drinking whiskey at a bar. Each should be extinguished in order to assure the generality of the treatment. Although the alcoholic should be encouraged to drink alcohol in the extinction sessions, there should be no social reinforcement for doing so.

The number of extinction sessions required for each patient will depend upon the severity of his or her alcoholism and the number of specific drinking situations in which the alcohol-drinking response must be extinguished. The duration of the extinction program may therefore range from about 1 to 5 weeks.

Once the alcohol-drinking response has been sufficiently weakened, the final extinction sessions could be conducted along with an element of punishment. Examples of punishment include mild electric shock when the alcohol is consumed, production of conditioned taste aversion from very large doses of alcohol with or without emetics, aversion therapy with an alcohol-sensitizing compound such as disulfiram or cyanamide, and the like.

After the final extinction session, the patient is told to abstain from all alcohol in the future. Various procedures can then be used to help ensure that the patient does in fact refrain from drinking alcohol. Such procedures include counselling, psychotherapy, family therapy, job therapy, joining Alcoholics Anonymous and the like. Efforts should also be taken to help the patient resume a normal productive life.

The patient should also be informed that although his or her alcohol-drinking response has been extinguished in the most frequently used drinking situations, it is possible that some have been missed. Consequently, if the patient anticipates or is experiencing a situation in which the response has not been extinguished, he or she should request additional extinction sessions involving this new situation. Alternatively, the patient could be kept on a maintenance program with continued administration of the opiate antagonist.

The opiate antagonist is administered according to the present invention by transdermal delivery. The present invention provides a means, or device, suitable for the rapid, easy and foolproof transdermal delivery of the opiate antagonist. The device is a package containing a fixed dose of antagonist, a vehicle and a permeation enhancer to assure rapid systemic delivery of the antagonist.

The package contemplated is a container, such as a capsule, sachet, or squeeze tube, holding a fixed volume of an ointment containing the antagonist, vehicle and enhancer. The alcoholic simply opens the container and massages all of the ointment inside into the skin. As demonstrated in Example 1, people automatically massage a fixed volume of ointment onto a fixed area of skin. Because the skin area covered by the ointment determines the rate of transdermal diffusion, a package containing a fixed volume of ointment can be used to deliver reliably a specific dose of antagonist systemically.

A very large skin area, e.g., an entire arm with an area of 100 cm$^2$, can be used with this procedure. There are a wide variety of vehicles and permeation enhancers that can provide transdermal diffusion of an antagonist across such large areas sufficient for the systemic doses needed for the extinction procedure with a lag time of less than one hour (see Example 2). Many could deliver the entire higher dose specified for naloxone (30 mg) in one or two hours. Sufficient quantities of naloxone to block alcohol reinforcement would still be present at the end of an evening session, 4–7 hrs later, but there would not be active amounts the next morning.

DESCRIPTION OF THE PREFERRED EMBODIMENTS

Various packages are possible for containing a fixed dose of opiate antagonist, vehicle, and permeation enhancer, e.g., a sachet, such as those presently used in delivery of individual amounts of shampoo, or a very small squeeze tube. The preferred embodiment, however, is a soft capsule which ruptures when pressed against the skin (FIG. 1). This releases the ointment directly onto the skin and the patient then massages it into the skin.

Rupturing capsules of this sort are currently used for applying cosmetics. For example, Revlon markets a product in which rupturing capsules are used for applying a sun-tanning lotion. Rupturing capsules, however, are not believed to have been previously suggested as a means of delivering therapeutic agents for systemic administration via transdermal diffusion. They have the advantage of being very easy to use and almost automatically delivering the entire contents to the skin with little possibility for loss from spillage.

Although it would not be dangerous if the patient accidentally took a capsule containing naloxone orally, this possibility could be precluded by making the capsules too large or of a shape that would prevent them from being swallowed. The capsule can be composed of gelatin, polymer film, or another material that is impervious to lipids and is easily ruptured by pressure against the skin.

The capsule would be very easy and safe to use. Spillage, which would be a problem with opening a sachet, is avoided because the act of rupturing the capsule against the skin automatically places the contents directly onto the skin. Another problem with both sachets and squeeze tubes is that care must be taken to assure that the entire contents are removed and applied. The capsule, however, releases all of its contents while it, along with the ointment, are being rubbed over the skin.

The capsule can be formed to hold a fixed volume of ointment, ranging from 0.001 to 2 ml, but preferably from 0.05 to 1 ml. If naloxone is used as the antagonist, the total amount of naloxone inside each package could range from 0.2 to 40 mg. A single package could be made to deliver the entire dose. Alternatively, packages with smaller amounts could be used and before each session the patient would be given the number of packages needed to add up to the desired total dose.

Figure 1B:
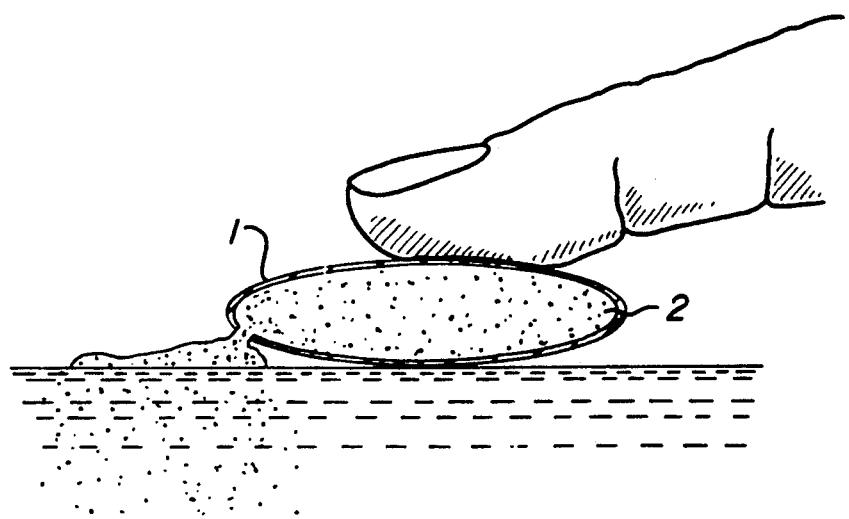

FIG. 1 illustrates the use of a capsule as a means for transdermal delivery of an opiate antagonist in the extinction procedure. FIG. 1 shows a cross-sectional view of a rupturable capsule. FIG. 1(A) shows the soft capsule 1 containing an ointment 2 composed of a fixed dose of an opiate antagonist, a vehicle, and a permeation enhancer, on the skin of a patient. FIG. 1(B) illustrates how pressing the capsule against the skin causes it to rupture, releasing the ointment directly onto the skin.

Although various opiate antagonists could be delivered by transdermal delivery according to the present invention, naloxone is contemplated to be the preferred antagonist because it matches the other requirements for the extinction procedure, because oral delivery does not produce reliable systemic concentrations due to high first-pass metabolism, and because it is currently approved for therapeutic use. Naloxone could be in the form of the acid, the base, or the salts thereof. The concentrations of naloxone in the ointment can range from 1 mg/ml up to or in excess of the solubility limit of the vehicle.

Possible vehicles include propylene glycol, isopropanol, ethanol. oleic acid, N-methylpyrrolidone, sesame oil, olive oil, wood alcohol ointments, vaseline, a triglyceride gel sold under the trade name Softisan 378, and the like.

Possible permeation enhancers include saturated and unsaturated fatty acids and their esters, alcohols, acetates, monoglycerides, diethanolamides and N,N-dimethylamides, such as linolenic acid, linolenyl alcohol, oleic acid, oleyl alcohol, stearic acid, stearyl alcohol, palmitic acid, palmityl alcohol, myristic acid, myristyl alcohol, 1-dodecanol, 2-dodecanol, lauric acid, decanol, capric acid, octanol, caprylic acid, 1-dodecylazacycloheptan-2-one sold under the trade name Azone by Nelson Research and Development, ethyl caprylate, isopropyl myristate, hexamethylene lauramide, hexamethylene palmitate, capryl alcohol, decyl methyl sulfoxide, dimethyl sulfoxide, salicylic acid and derivatives, N,N-diethyl-m-toluamide, crotamiton, 1-substituted azacycloalkan-2-ones, polyethylene glycol manolaurate, and other compounds compatible with the package and the antagonist, and having transdermal permeation activity. In accord with patent EPA-0282156, corticosteroid or other agents to lessen skin irritation could also be included. Currently, the preferred vehicle is propylene glycol and the preferred enhancer is linolenic acid (10%).

EXAMPLE 1

The rate of transdermal drug delivery, unless otherwise controlled, is proportional to the area of skin to which it is applied. The skin area affected by a topical bandage is determined simply by the size of the bandage. The use of the rupturing capsules, as well as sachets and the like however, is dependent upon whether a fixed volume of ointment reliably covers a fixed area of skin.

Consequently, experiments were conducted in order to determine whether the volume of ointment reliably controls the skin area onto which subjects automatically massage it. The same ointment (Hydroderm, from Erisan, Espoo, Finland) was used in each experiment. A small, randomly determined, amount of ointment, was weighed, then massaged by hand into the skin in a natural manner, and then the area covered was measured.

In the first experiment, one subject applied 10 quantities onto skin areas on the arm and stomach over a 2 day period, never using the same area twice on the same day. In the second experiment, 7 subjects (3 male, 4 female) had a measured amount of ointment applied to their right forearm (underside) by the experimenter and then the subject self-administered a second quantity to their own left forearm. The subjects were given no instructions except to make the area roughly rectangular and continuous in order to facilitate measurement.

The mean ($\pm$SE) coverage found in the first experiment was 1.1 $\pm$0.2 cm$^2$ of skin per mg of ointment; in the second, applied by the experimenter, 1.0 $\pm$0.1 cm$^2$/mg, and applied by the subjects, 0.9 0.1 cm$^2$/mg; and for all 24 measurements, 1.0 $\pm$0.1 cm$^2$/mg. There was no significant difference in the second experiment between coverages produced when the experimenter applied the ointment and when the subjects self-administered it (t=0.74, 6 df, p>0.40). The overall correlation between quantity of ointment and area covered was r=0.98.

The high correlation and the small standard errors indicate that a fixed quantity of a specific ointment can be relied upon to cover a relatively fixed area of skin. They also indicate that there is essentially no difference between having application done by another person and having subjects do it themselves, and that no special instructions need to be given to the subjects.

There were individual differences in the amount of coverage, probably dependent upon skin type: the correlation between the cm$^2$/mg produced by experimenter application and subject application was r=0.81 (5 df, p<0.05). The magnitude of the differences between subjects was so small that it would have little effect upon the amount of drug being delivered systemically, but it could, nevertheless, be taken into consideration when choosing which fixed volume to be given to the patient.

EXAMPLE 2

The following example is generated from the findings in Example 1 plus the experimental results with the hairless mouse disclosed by Aungst et al (U.S. Pat. No. 4,626,539). Results from this animal model have been found to allow "reasonable estimations of human skin permeability" (Merkle, H.P. *Methods and Findings in Experimental and Clinical Pharmacology*, 11:135–153, 1989).

A 1 ml rupturing capsule (or sachet, squeeze tube, and the like) containing 30 mg of naloxone in a vehicle of propylene glycol, with 10% (v/v) linolenic acid as the permeation enhancer could be given to patients. Assuming the coverage is similar to that of Hydroderm, this would cover a skin area of 900–100 cm$^2$ when self-applied by the patients, i.e., approximately the area of one arm. In the hairless mouse, this same ointment produced a naloxone flux of 322 $\mu$g/cm$^2$/hr. The delivery in humans should be similar but slightly faster, and with a skin area of 900–1000 cm$^2$ should deliver systemically about 5 mg/min. Even with the reported lag time (in the mouse) of 18 min, this should deliver the entire 30 mg of naloxone systemically in half an hour, at which time the extinction session could begin.

The patients could massage the ointment onto their own arms early in the evening and then go to the location where alcohol would be drunk. Sufficient amounts of naloxone to block alcohol reinforcement would still be present at the end of the session 4–7 hrs later. By the next morning, however, essentially all of the naloxone would have been metabolized, and thus there would be no effect on other responses made during the day.

Although the invention has been described in detail and with reference to specific embodiments thereof, it will be apparent to one skilled in the art that various changes and modifications can be made therein without departing from the spirit and scope thereof.

What is claimed is:

1. A method for treating alcoholism by extinguishing the alcohol-drinking response, comprising the steps of:
   transdermally administering to a subject suffering from alcoholism, an opiate antagonist selected from the group consisting of naloxone, naltrexone, cyclazocine, diprenorphine, etazocine, levalorphan, metazocine, nalorphine, and salts thereof, in a daily dosage sufficient to block the stimulatory effect of alcohol, said opiate antagonist being administered by a transdermal delivery means containing a fixed dose of the antagonist, a vehicle and a permeation enhancer;
   while the amount of antagonist in the subject's body is sufficient to block the stimulatory effect of alcohol, having the subject drink an alcoholic beverage; and
   continuing the steps of administration of the opiate antagonist and drinking of an alcoholic beverage until the alcohol-drinking response is extinguished.

2. The method of claim 1 further comprising, after the alcoholic beverage is consume, administering to the subject electric shock an emetic, or an alcohol sensitizing compound.

3. The method of claim 2 wherein the alcohol sensitizing compound is disulfiram or cyanamide.

4. The method of claim 1 further comprising continuing the administration of an opiate antagonist after the alcohol-drinking response is extinguished.

5. The method of claim 1 wherein the transdermal means is a capsule that is easily rupturable when pressed against the skin.

6. The method of claim 5 wherein the volume of the capsule is in the range of 0.001 to 2 ml.

7. The method of claim 1 wherein the transdermal means is a sachet or squeeze tube with a net volume ranging from 0.05 to 2 ml.

8. The method of claim 1 wherein the opiate antagonist is naloxone and the fixed dose is 0.2 to 40 mg.

9. The method of claim 1 wherein the opiate antagonist is naltrexone and the fixed dose is 20 to 300 mg.

10. The method of claim 1 wherein the vehicle is selected from the group consisting of propylene glycol, isopropanol, ethanol, oleic acid, N-methylpyrrolidone, sesame oil, olive oil, wood alcohol ointments, vaseline, and triglyceride gel.

11. The method of claim 1 wherein the permeation enhancer is selected from the group consisting of saturated and unsaturated fatty acids and their esters; alcohols; acetates; monoglycerides, diethanolamides and N,N-dimethylamides.

12. The method of claim 11 wherein the permeation enhancer is selected from the group consisting of linolenic acid, linolenyl alcohol, oleic acid, oleyl alcohol, stearic acid, stearyl alcohol, palmitic acid, palmityl alcohol, myristic acid, myristyl alcohol, 1-dodecanol, 2-dodecanol, lauric acid, decanol, capric acid, octanol, caprylic acid, 1-dodecylazacycloheptan-2-one, ethyl caprylate, isopropyl myristate, hexamethylene lauramide, hexamethylene palmitate, capryl alcohol, decyl methyl sulfoxide, dimethyl sulfoxide, salicylic acid and derivatives, N,N-diethyl-m-toluamide, crotamiton, 1-substituted azacycloalkan-2-ones, and polyethylene glycol manolaurate.

* * * * *

UNITED STATES PATENT AND TRADEMARK OFFICE
CERTIFICATE OF CORRECTION

PATENT NO. : 5,096,715
DATED : March 17, 1992
INVENTOR(S) : John D. SINCLAIR

It is certified that error appears in the above-identified patent and that said Letters Patent is hereby corrected as shown below:

Column 5, line 35, "!" should read -- 1 --;

line 43, "100 $cm^2$" should read -- 1000 $cm^2$ --.

Column 7, line 46, "0.9 0.1 $cm^2$/mg;" should read -- 0.9 ± 0.1 $cm^2$/mg; --.

Column 8, line 19, "900-100 $cm^2$" should read -- 900-1000 $cm^2$ --.

Column 8,

Claim 2, line 2, "consume," should read -- consumed, --;

line 3, "shock" should read -- shock, --.

Signed and Sealed this

Fourteenth Day of September, 1993

Attest:

BRUCE LEHMAN

*Attesting Officer*   *Commissioner of Patents and Trademarks*